(12) United States Patent
Chakravarthy

(10) Patent No.: US 10,413,451 B2
(45) Date of Patent: Sep. 17, 2019

(54) WOUND DRESSING

(75) Inventor: Debashish Chakravarthy, Vernon Hills, IL (US)

(73) Assignee: Medline Industries, Inc., Mundelein, IL (US)

( * ) Notice: Subject to any disclaimer, the term of this patent is extended or adjusted under 35 U.S.C. 154(b) by 0 days.

(21) Appl. No.: 12/652,964

(22) Filed: Jan. 6, 2010

(65) Prior Publication Data

US 2010/0204667 A1   Aug. 12, 2010

Related U.S. Application Data

(60) Provisional application No. 61/142,855, filed on Jan. 6, 2009.

(51) Int. Cl.
*A61F 13/02* (2006.01)

(52) U.S. Cl.
CPC ...... *A61F 13/0279* (2013.01); *A61F 13/0203* (2013.01)

(58) Field of Classification Search
CPC .... A61L 15/58; A61F 13/02; A61F 13/00029; A61F 13/00; A61F 13/00042; A61F 13/0209; A61F 2013/00217; A61F 2013/00604
USPC ................ 602/41–59, 78; 604/304, 307, 308
See application file for complete search history.

(56) References Cited

U.S. PATENT DOCUMENTS

| | | | |
|---|---|---|---|
| 4,909,243 A | 3/1990 | Frank et al. | |
| 5,259,835 A | 11/1993 | Clark et al. | |
| 5,702,715 A | 12/1997 | Nikolaychik et al. | |
| 6,695,515 B1 | 2/2004 | Fleury | |
| 7,066,934 B2 | 6/2006 | Kirsch | |
| 9,750,838 B2 | 9/2017 | Duncan et al. | |
| 10,201,631 B2 | 2/2019 | Duncan et al. | |
| 2003/0153860 A1* | 8/2003 | Nielsen ............... | A61F 13/0203 602/43 |
| 2003/0180493 A1 | 9/2003 | Hirashima et al. | |
| 2004/0127835 A1 | 7/2004 | Sigurjonsson et al. | |

(Continued)

FOREIGN PATENT DOCUMENTS

| | | |
|---|---|---|
| EP | 0353972 | 1/1994 |
| JP | 2-74252 A | 3/1990 |

(Continued)

OTHER PUBLICATIONS

Office Action for U.S. Appl. No. 14/664,264, dated Sep. 30, 2015, 21 pages.

(Continued)

*Primary Examiner* — Ophelia A Hawthorne
*Assistant Examiner* — Caitlin A Carreiro

(57) ABSTRACT

A composite wound dressing includes an absorbent portion coupled to the vapor permeable backing with a first adhesive and a wound contact portion having a first portion coupled to the absorbent portion with a second adhesive, and the wound contact portion having a second portion coupled to the vapor permeable backing with the first adhesive is disclosed. Further a skin securement portion coupled to the backing portion with the first adhesive, the skin securement portion including a semi-self adherent adhesive, and a void having a first size, wherein at least a portion of absorbent is accessible through the void. The wound contact portion has a size greater than the first size of the void.

21 Claims, 11 Drawing Sheets

(56) References Cited

U.S. PATENT DOCUMENTS

| | | | |
|---|---|---|---|
| 2004/0133143 A1* | 7/2004 | Burton | A61F 13/0203 602/58 |
| 2005/0240221 A1 | 10/2005 | Dunshee | |
| 2005/0245855 A1 | 11/2005 | Brothers | |
| 2007/0041935 A1 | 2/2007 | Salamone et al. | |
| 2008/0154168 A1 | 6/2008 | Lutri | |
| 2010/0159192 A1 | 6/2010 | Cotton | |
| 2013/0012858 A1 | 1/2013 | Jackson et al. | |
| 2013/0018336 A1 | 1/2013 | Pernot | |
| 2013/0237895 A1 | 9/2013 | Rastegar et al. | |
| 2013/0303654 A1 | 11/2013 | Salamone | |
| 2015/0265741 A1 | 9/2015 | Duncan et al. | |

FOREIGN PATENT DOCUMENTS

| | | |
|---|---|---|
| JP | 6-509966 A | 11/1994 |
| JP | 2008-220437 A | 9/2008 |
| JP | 2009-504342 A | 2/2009 |
| JP | 2014-506176 A | 3/2014 |
| WO | WO 02/02177 A1 | 1/2002 |
| WO | WO 2006/127385 A2 | 11/2006 |
| WO | WO 2012/094648 A1 | 7/2012 |
| WO | WO 2013/076450 | 5/2013 |
| WO | WO 2015/143341 | 9/2015 |

OTHER PUBLICATIONS

International Search Report and Written Opinion for International Application No. PCT/US2015/021782, dated Jun. 18, 2015.
Rippon et al., "Skin adhesives and their role in wound dressings," Wounds UK, 2007, vol. 3, No. 4, pp. 76-86.
Supplementary European Search Report for European Application No. 15764414.7, dated Oct. 2, 2017, 6 pages.

* cited by examiner

WOUND DRESSING

CROSS-REFERENCE TO RELATED APPLICATION

This application claims the benefit of U.S. Provisional Application No. 61/142,855, filed Jan. 6, 2009, which is hereby incorporated by reference in its entirety.

FIELD OF THE DISCLOSURE

The present disclosure relates generally to wound dressings and more particularly to trauma reducing highly absorbent and breathable wound dressings, for example, topical dressings for use in wound care.

BACKGROUND OF THE DISCLOSURE

In the past many wound dressings included an absorbent material and an adhesive to secure the dressing to the wound. The adhesive portion allows the absorbent material to stay substantially in contact with the wound by adhering to the region of the body surrounding the wound, typically the skin. The adhesive portion however needs to be strong enough to secure the dressing to the wound for an extended period of time, yet still release from the skin after use. These adhesives however can have a traumatizing effect when the dressing is removed. As the dressing is removed, the force required to separate the adhesive from the skin may cause pain and discomfort to the dressing wearer as the skin and hair are subjected to yanking or pulling and stretching.

Some wound dressings apply a trauma reduced adhesive, such as a silicone based adhesive, to reduce the trauma associated with the release of the dressing from the wound site. For example, the characteristics of polymerized siloxanes such as silicone gels allow the dressing to remain secured to the wound region yet require less pull force to remove the dressing resulting in reduce trauma during the release. Some wound dressings have a silicone gel covering the entire dressing including the wound contact portion to secure the absorbent material to the wound. However, silicone adhesives on dressings when in a continuous layer provide very low moisture vapor transmission rate (MVTR) of the dressing. This leads to increased perspiration, poor breathability of the wound and as a result increased healing time. The dressing needs to remain on the wound as long as possible to reduce infection yet be breathable enough to prevent or reduce skin maceration also leaving the wound more vulnerable to infection. One method incorporated into current dressings to improve the MVTR is to discontinuously or selectively apply the silicone based adhesive to the dressing in one fashion or another. In one application the silicone adhesive is applied to the foam so as to contact the wound.

However, covering the wound contact portion of the dressing with silicone reduces the absorbency rate of the dressing. This leads to a slower rate of absorption over time, increasing the chances of maceration in the peri wound area.

Applying the silicone adhesive to the backing and then securing a foam pad to the backing with the silicone, as with a typical "island" type dressing, results in poor adhesion of the foam to the backing. This is particularly the case once the foam becomes wet and the adhesion characteristics of the silicone to the foam is reduced and the foam separates from the backing.

Some dressings incorporate a superabsorbent material to increase the amount of fluid retainable by the dressing thereby decreasing the amount in the wound and thus improving the healing ability of the dressing. This may further reduce the number of dressing changes and potentially reducing dressing change trauma, plus infection of the wound as with each dressing change and exposure to the environment, chances of infection increase.

Further, absorbent material, and more particularly super absorbent material, can be unpleasant feeling to the user when put in direct contact with the skin, particularly for long periods of time and even more so once the absorbent material becomes wet.

Another problem is that absorbent/SAP materials, which usually consist of superabsorbent particles bonded to a carrier layer, tend to swell exuberantly, in particular the superabsorbent particles loosen from the carrier as they fill with exudates being expressed by the wound.

Thus, there is a need for a non traumatizing wound dressing that has a large super absorbent area with high MVTR at the wound contact region and that maintains its structure when wet.

The various aspects, features and advantages of the disclosure will become more fully apparent to those having ordinary skill in the art upon careful consideration of the following Detailed Description thereof with the accompanying drawings described below.

DETAILED DESCRIPTION

Figure 1:
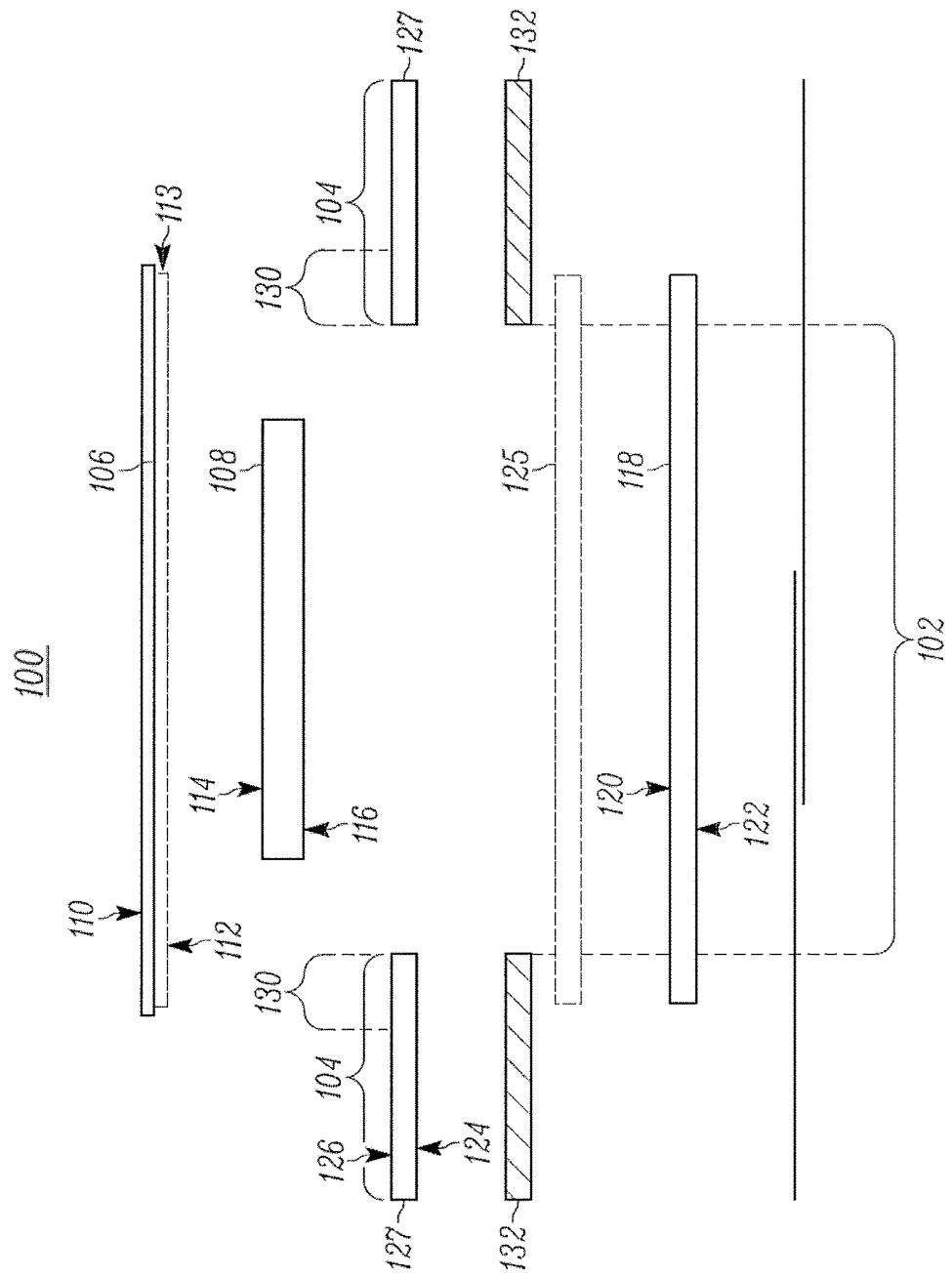
FIG. 1 is an exploded cross sectional view of one example of a multiple layer wound dressing.

Before describing in detail embodiments that are in accordance with the present invention, it should be observed that the embodiments reside primarily in combinations of apparatus components and method steps for a wound dressing. Accordingly, the apparatus components and method steps have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

In describing the embodiments of the invention in detail and referring to the drawings, like numbers indicate like parts throughout the figures. As used in the description herein and throughout the claims, the following terms take the meanings explicitly associated herein, unless the context clearly dictates otherwise: the meaning of "a," "an," and "the" includes plural reference, the meaning of "in" includes "in" and "on." Relational terms such as first and second, top and bottom, and the like may be used solely to distinguish one entity or action from another entity or action without necessarily requiring or implying any actual such relationship or order between such entities or actions.

Embodiments of the invention provide a wound dressing that has a absorbent portion and a skin friendly securement portion that is a skin contact layer with a semi-self adhering adhesive border. In so doing, embodiments of the invention work to provide high absorbency with high breathability yet strong adhesive properties with reduced trauma during release of the dressing. This leads to an increased healing rate and improved comfort. In the embodiment, there is maximization of the use of the beneficial aspects of the material (e.g. maximizing the superabsorbent size, and leveraging the dimensions of the silicone border), and a minimization of the reduction of the effectiveness of the components in the dressing, thereby also minimizing the cost of the dressing.

In one embodiment, the dressing incorporates a superabsorbent material. The superabsorbent material increases the fluid retention capacity of the dressing over absorbent materials of the past. In this embodiment the super absorbent is configured between a wound contact portion, a foam layer, and a liquid impervious backing layer.

In another embodiment the superabsorbent material is configured between two foam layers. A first foam layer and a second foam layer. The first foam layer has a first foam side that is adjacent to the superabsorbent and a second foam side that is a skin facing foam side. The second foam layer has a first foam side that is adjacent to the super absorbent and a second side that is adjacent to a backing of the dressing.

In yet another embodiment, the absorbent material is configured in an outer casing or sachet, which may be a non-absorbent containment material such as a polyethylene, polypropylene, polyester, copolyester, individually or any combination thereof, or any material that is flexible and fluid permeable, preferably in a polymeric form. In this embodiment, the sachet is coupled to the backing with a first adhesive layer and to the foam with a second adhesive layer.

Figure 2:
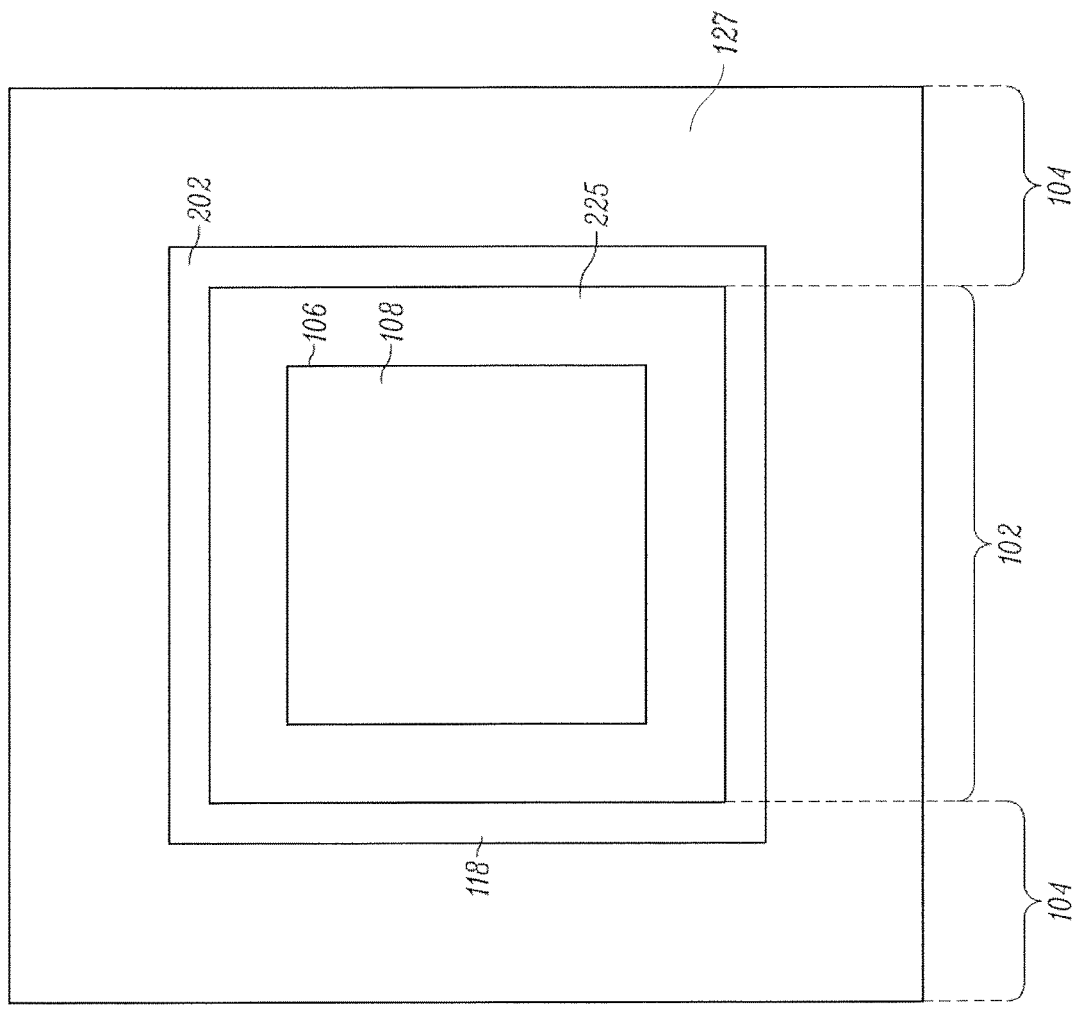
FIG. 2 is a top view of one example of a multiple layer wound dressing.
Figure 3:
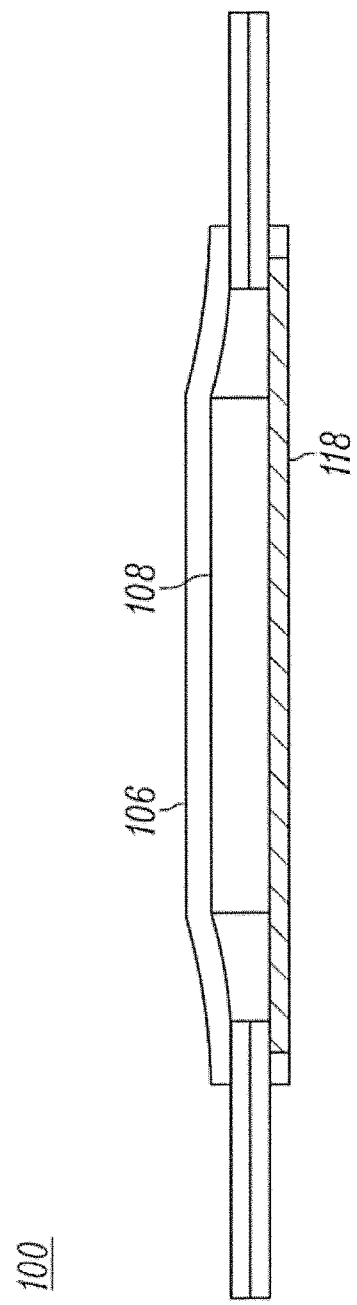
FIG. 3 is a cross sectional view of one example of a multiple layer wound dressing.

One embodiment of the dressing is illustrated in FIG. 1 through FIG. 3. FIG. 1 illustrates an exploded cross sectional view of one exemplary composite atraumatic wound dressing 100; FIG. 2 illustrates a top view of the exemplary dressing; and FIG. 3 illustrates a cross sectional view of the dressing 100. The dressing 100 is a composite as it comprises a plurality of layers bound together. The dressing 100 comprises an absorbent portion 102 and a non-absorbent portion 104. The non-absorbent portion 104 is a skin securement portion 104 that contacts the skin adjacent to the wound to secure the dressing and hence absorptive portion to the wound. The non-absorbent portion 104 is flexible and as pliable as possible to provide comfort to the user. Stiff edges at or near the border, or peripheral edge of the dressing 100 reduce the comfort to the user as the dressing 100 does not flex as well with the movement of the skin.

The dressing 100 comprises a barrier layer 106 material, that is liquid impervious yet moderate to highly breathable, i.e. having a moderate to high moisture vapor transmission rate (MVTR)>300 gm/m2/24 hours, coupled to an absorbent layer 108 material also having a high MVTR. The barrier layer 106 has a first barrier side 110 and a second barrier side 112. The barrier layer 106 may include polyurethane, polyester, polyvinyl chloride, copolymers or combinations thereof or the like. For example, in this embodiment, the barrier layer 106 is a polyurethane film. Also in this embodiment, the barrier layer 106 is coated with a first adhesive 113, which is a barrier adhesive 113 on at least one side of the barrier layer 106, and in this embodiment is coated on the second barrier side 112. Further, in this embodiment, the barrier adhesive 113 covers a substantial portion of the second barrier side 112, however in other embodiments the barrier adhesive may be selectively applied to portions of the barrier layer 106.

The dressing 100 further comprises an absorbent layer 108, which may also be referred to as an absorbent core. The absorbent layer 108 has a first absorbent side 114 and a second absorbent side 116. The absorbent layer 108 may be substantially flat (i.e. planar), having an "x" and "y" dimension that is greater than a "z" dimension. The absorbent layer 108 may be comprised of at least one layer of absorbent material or a plurality of layers of absorbent material or a plurality of absorbent material types. The second barrier side 112 is adjacent to the first absorbent side 114 and the two layers are coupled together by the first adhesive 113. In this embodiment, the second barrier side 112 of the barrier layer 106 is greater in size, in both the "x" and "y" dimensions than the absorbent layer 108. The barrier layer 106 and the absorbent layer 108 are configured such that at least a portion of each of the layers are adjacent and in one embodiment are planarly adjacent. Planarly adjacent means geometric planes in space next to one another wherein the planes are at least substantially parallel.

A wound contact portion 118, also known as cushion layer 118, of the dressing is adjacent to the wound and potentially adjacent skin and is a cushion layer material which is configured adjacent to the second absorbent side 116 of the absorbent layer 108 material. The cushion layer 118 having a first cushion side 120 and a second cushion side 122. The first cushion side 120 is adjacent to the second absorbent side 116. The second cushion side 122, has at least portions thereof that contact the patients skin and more particularly the wound such that the second cushion side 122 of the cushion layer 118 provides a comfortable tactile feel to the individual wearing the dressing 100. The cushion layer 118 may be greater in size than the absorbent portion 108. In the embodiment illustrated in FIG. 1, the absorbent layer 108 is 40 percent less than the size of the cushion layer 118. However it is to be understood that 40 percent is one exemplary embodiment and is in not intended to limit the ratio of the size of the absorbent layer 108 to the size of the cushion layer 118. For example the ratio may be as high as 70 percent coverage.

In this embodiment the cushion layer 118 is made of a foam material. The cushion layer 118 may also be made of a woven material or a non woven material or a combination thereof. In this embodiment the cushion layer 118 is a foam that provides a cushion to the absorbent layer 108, providing a more comfortable feel to the user. The cushion layer 118 further may have a liquid wicking characteristic that allows liquid to flow into the absorbent core 108 of the dressing while the absorbent core layer 108 prevents the liquid from drain back out of the dressing through the foam, thereby locking in substantial portions of the liquid. The word "liquid" is used in general to describe material that comes from a wound, i.e. wound exudates such as blood and related material.

Referring to FIG. 1 and FIG. 2, the skin securement portion 104 is coupled to the barrier layer 106. The skin securement portion 104 comprises a border layer and a void 225 in the boarder border layer 127. The void 225 in the securement portion 104 allows the skin securement portion 104 to surround the absorbent portion 102 including the absorbent layer 108 and at least a portion of the cushion layer 118. In one embodiment the securement portion 104 is outside of a cushion layer perimeter 202, while in another embodiment, the cushion layer perimeter 202 is adjacent to both the void 225 and overlaps a portion of the skin securement portion 104 which is adjacent to the void 225. The void 225 in the skin securement portion 104 provides an opening to allow liquid to have access to the absorbent layer 108, such that the absorbent layer 108 is configured within the void 225 and adjacent to the barrier layer 106. The border layer 127 borders and extends away from at least a portion of the absorbent portion 102. The skin securement portion is covered at least partially and on at least one side by a second adhesive 132 which is a skin securement adhesive 132. The second adhesive 132 may be continuously or discontinuously coated on the border layer, or a combination thereof.

The border layer 127 includes a first border side 126 and a second border side 124. The first border side 126 has at least a barrier contacting portion 130 where the border layer 127 is coupled to the barrier layer 106. The second border side 124 is a skin contacting border side. The second adhesive 132 is applied to at least portions of the second border side 124; the second adhesive 132 adheres to both skin and the border layer 127 material. The second adhesive 132 releasably secures the dressing 100 to the user. The second adhesive 132 may substantially remain on the second border side 124. When the dressing 100 is soiled, the dressing is removed from the skin by peeling the border layer 127 away from the skin overcoming the second adhesive 132. The second adhesive 132 may be a non-traumatic adhesive. A non-traumatic adhesive requires less force to separate from the skin than a traumatic adhesive, reducing the amount of discomfort or pain to the user as the dressing is removed. The second adhesive may be a non self adherent or a semi self adherent adhesive such as a silicone based adhesive gel. In one embodiment the securement portion comprises a flexible polymer substrate such as a copolyester substrate up on which a silicone gel is applied to the skin facing side.

In one embodiment the cushion layer 118 is centered relative to the void 225 and has a size smaller than the void 225 such that the skin securement portion 104 may completely surround the cushion layer 118 with a gap between the skin securement portion 104 and the cushion layer 118. In another embodiment, the cushion layer 118 is greater in size than the void 225 in at least one dimension. In this embodiment, the cushion layer 118 overlaps the second border side 124 of the border layer 127, adjacent to the void 225, such that the first cushion side 120 of the cushion layer 118 is on the second border side 124 as shown in FIG. 3. Said in another way, the second border side 124 of the border layer 127, at the overlap, is in contact with the non skin contact first cushion side 120. The larger cushion layer in this embodiment increases the possibility that all exudates with will transfer through the cushion layer 118 to the absorbent layer 108. The smaller the cushion layer the greater the chance that the wound exudates will transfer to the absorbent from outside the cushion layer 118.

In one embodiment, the second adhesive 132 is a semi-self adherent adhesive such as silicone or a silicone gel. Silicone is one exemplary adhesive that is self adhesive but will release from itself under a relatively low amount of force. The silicone adheres to the border which may be a polyurethane (PU) or copolyester, or any other such film forming material such that a majority of the adhesive remains on the border after the dressing 100 is removed from the skin, with only residual amounts of silicone left on the skin. Other semi-self adherent adhesives, for example, include polyurethane gels, or other low tack acrylic adhesives and the like.

In one embodiment the plurality of layers of the multi-layer wound dressing 100 are coupled together by the first adhesive 113 of at least one adhesive type. The first adhesive 113 secures the layers together so that the dressing components do not separate during use as bodily fluid/exudates is absorbed into the absorbent portion 102 of the dressing 100. The first adhesive 113 may also prevent exudates from exiting the dressing beyond the barrier layer 106. The first adhesive 113 that secures the barrier layer 106 to the border layer 127 seals the dressing 100 such that exudates does not leak outside of the dressing or the leakage is minimized. The first adhesive layer 113 couples the barrier layer 106 to the absorbent layer 108, the first adhesive 113 also couples the barrier layer 106 to the cushion layer 118 outside the peripheral edges of the absorbent layer 108, and the first adhesive layer 113 couples the barrier layer 106 to the border layer 127 of the securement portion 104. The first adhesive may be a pressure sensitive adhesive, such as an acrylic adhesive or the like. Other adhesive, although not limited to, may be latex based adhesives, polyisobutylenes, polybutenes, polyolefins or the like. A third adhesive layer 125, which may be of the same type as the first adhesive layer, couples or secures the cushion layer 118 to the absorbent layer 108. In this embodiment, the third adhesive may also contact the second adhesive 132 of the border layer 127 and the first adhesive 113 of the barrier layer 106.

Still further the third adhesive 125 coupling the cushion layer 118 layer to the absorbent layer 108, surprisingly increases the effectiveness of the absorbent characteristics as the foam separation from the absorbent is minimized. Preventing the physical separation of the absorbent layer 108 from the cushion layer 118, improves overall esthetics of the dressing as well as the transfer of exudates from the wound bed to the absorbent layer as the layers remain in contact promoting the transfer. Further, preventing the separation, increases the contact surface area of the foam to the skin and the wound bed further increasing the rate at which exudates is removed from the wound and contained within the absorbent portion of the dressing 100. Further, it is also surprising that this configuration allows the superabsorbent to be relatively large compared to the void and the foam, greater than 30% of the foam area corresponding to the void in the silicone securement layer. This ensure that a substantial portion, that is greater than 30% and as high as 70% of the wound contact layer, is serviced by the absorbent layer 108 which is the maximization of the usage potential of the contact layer, which is an economic aim of the unique design.

The unique combination of the foam (i.e. cushion layer 118), adhesive, and super absorbent further promotes accelerated healing as the exudates is retained in the absorbent portion and not the foam, leaving the foam with less moisture and greater air circulation next to the skin and wound. In one embodiment, the foam remains dry to the touch on the second cushion side 122 while the absorbent layer retains a substantial amount of fluid.

Figure 4:
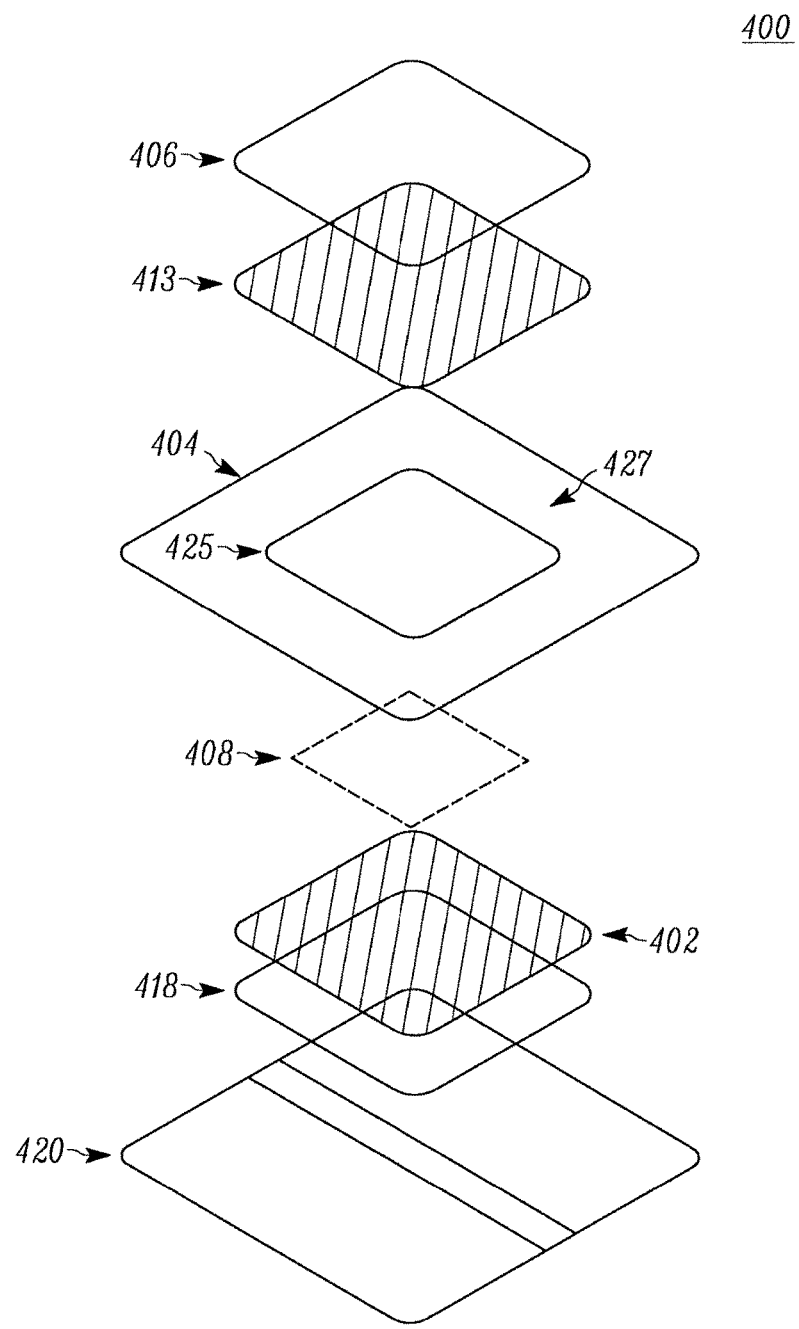
FIG. 4 is an exploded view of a composite wound dressing, according to an embodiment.

Moving to FIG. 4, an exploded view of another exemplary composite wound dressing 400 is shown. In this embodiment a backing layer 406 has a size of 3.125 inches square. The backing layer 406 has a first adhesive 413, which may be a continuous or discontinuous adhesive, coated thereon. The backing layer 406 is coupled to a border layer 427 with the first adhesive 413. The border layer has a skin contact side that has a second adhesive (not shown in FIG. 4) coated thereon. The border layer 427 has a peripheral edge 404 and an overall size of 5 inches square. The border layer 427 has a void 425 that has a size of 2.625 inches square. An absorbent layer 408 is coupled to the barrier layer 406 by the first adhesive 413. The absorbent layer has a size of 2.0 inches square. In this embodiment the absorbent is a super absorbent material. The super absorbent layer is coupled to a foam layer 418 by a third adhesive 402.

In this embodiment the third adhesive 402 used in the composite dressing, is a transfer adhesive. This further maintains the securement of the plurality of layers of the composite wound dressing 400. In this embodiment the transfer adhesive 402 couples the foam cushion layer 418 to the absorbent layer 408, the border layer 427 and the barrier layer 406 or the first adhesive 413 of the barrier layer 406. A release liner 420, which is a "butterfly" liner made up of two overlapping parts is removably applied to the dressing, adhering to the second adhesive, covering the dressing on one side in its entirety.

In yet another embodiment, a fourth adhesive which is a second transfer adhesive is used. The fourth adhesive, not shown, couples the barrier layer 406 and adhesive 413 to the border 427, the super absorbent 408 and the foam 418.

The absorbent layer may be a woven material, a mesh, net, pattern or the like. The absorbent layer may be a super absorbent material. A super absorbent material has polymeric absorbent particles, that when introduced to moisture, e.g. exudates, resist yielding the absorbed liquid under pressure.

The barrier material may be a polyurethane film, polyester polyamide, copolyester, or any film forming polymer or the like.

The cushion layer may be a foam, woven, non woven or the like. The cushion material may be a polyurethane, a polyethylene foam, a polyvinyl alcohol foam or the like. In one embodiment the cushion layer is a swellable foam layer. In another embodiment, the foam is a non swellable foam.

The border and the semi-self adhesive layer may be a polyurethane layer, or another film such as a copolyester, copolyamide, polyamide, polyethylene or any film forming polymer, with semi self adhering or non self adhering adhesive such as a silicone based gel adhesive coating.

In this embodiment the dressing 100 has a plurality of portions, each of which have a different moisture vapor transmission rate (MVTR). An absorbent portion 102 has a first MVTR and the skin securement portion 104 has a second MVTR. In one embodiment the first MVTR is more than 300 and the second MVTR is less than 300. MVTR may be measured using the units of $gm/m^2/24$ hours.

Figure 5:
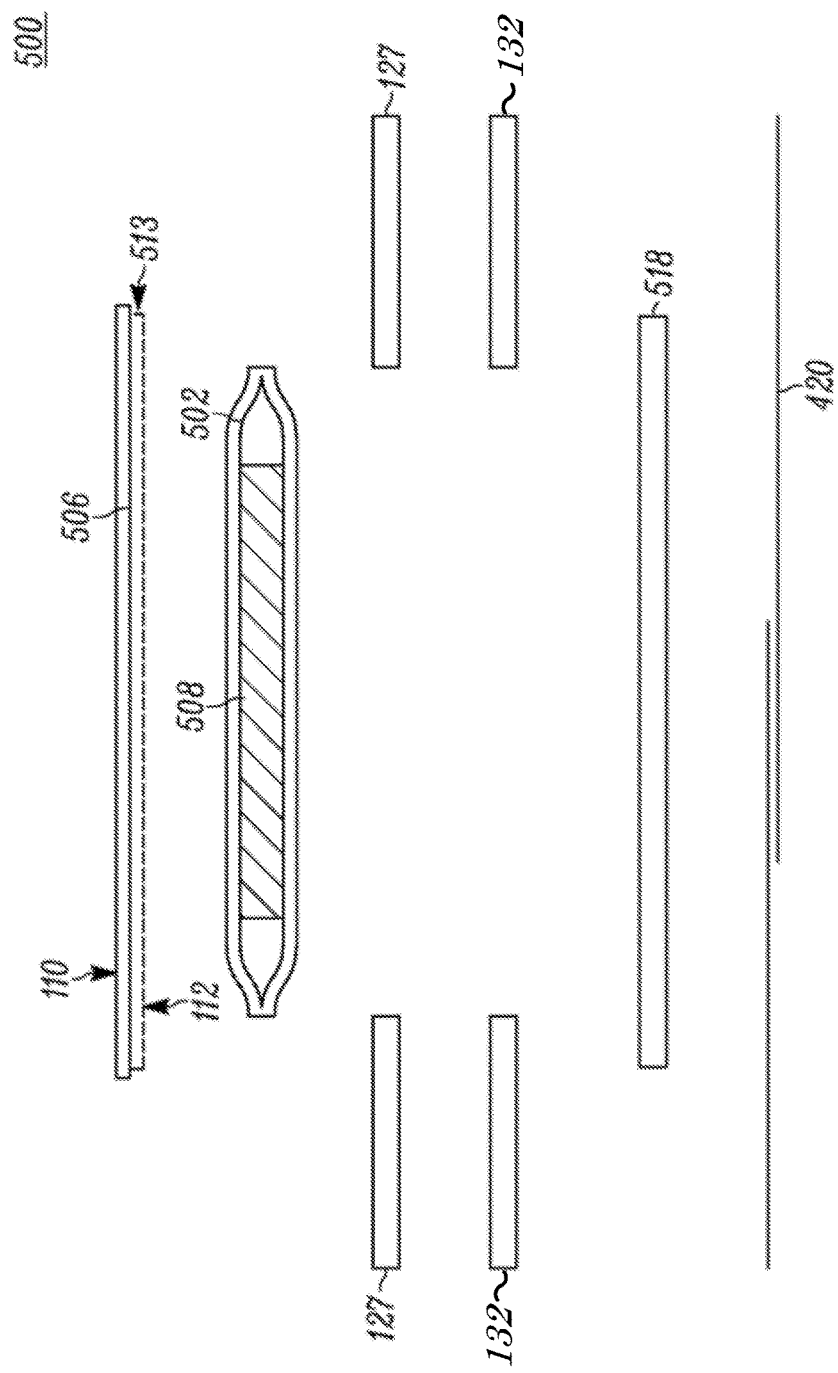
FIG. 5 is an exploded cross sectional view of one example of a multiple layer wound dressing.

In one embodiment, illustrated in FIG. 5, a composite dressing 500 comprises an absorbent material 508 carried in a sachet 502. In this embodiment the sachet encloses the absorbent material, which may also be a super absorbent material. The sachet is made of, fluid permeable materials, which may be absorbent or non absorbent material. In one embodiment the sachet comprises polypropylene. The sachet is coupled to the backing layer 506, by the first adhesive 513 and to the cushion layer 518 by the third adhesive, which may be a transfer adhesive.

Figure 6:
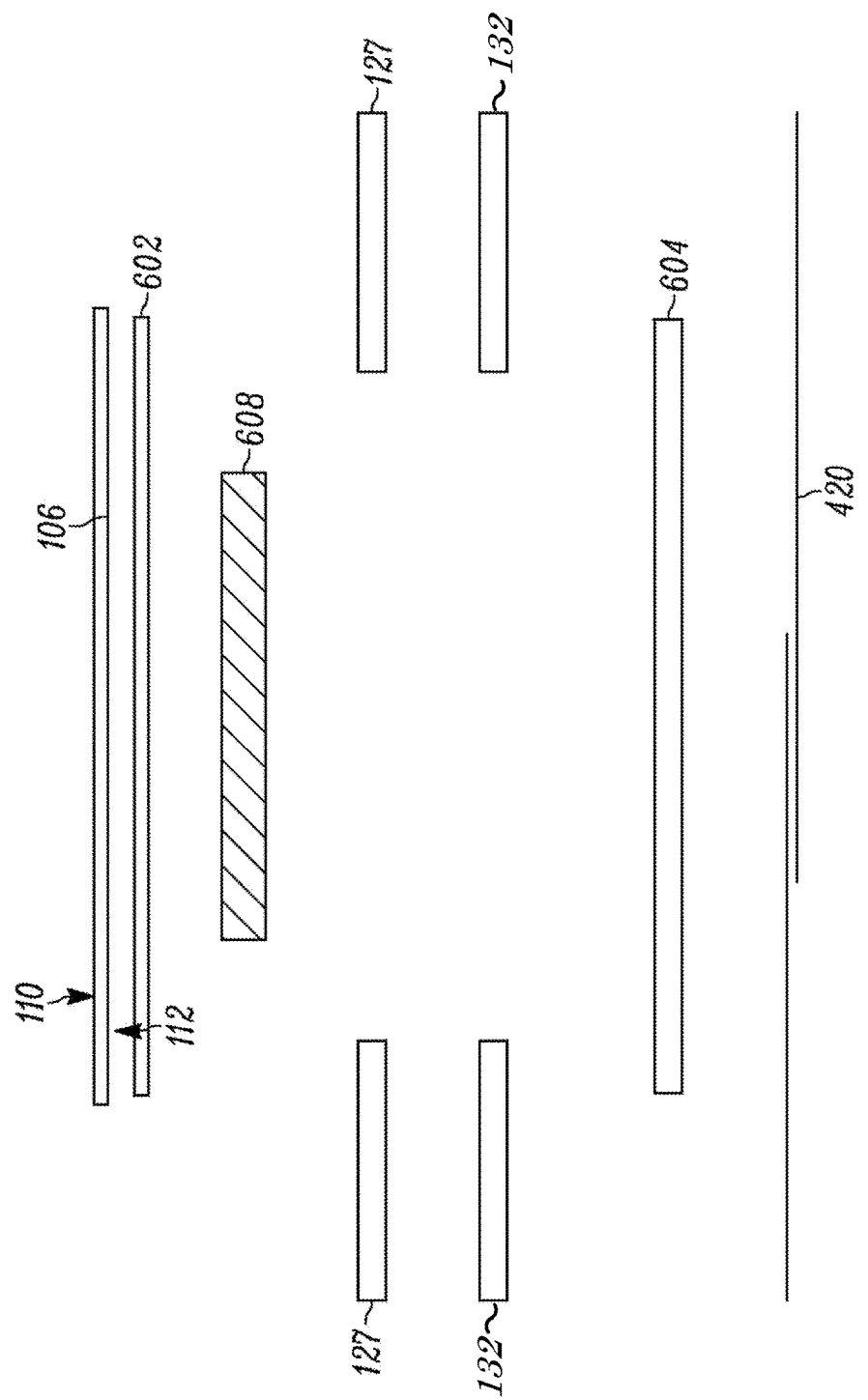
FIG. 6 is an exploded cross sectional view of one example of a multiple layer wound dressing.
Figure 7:
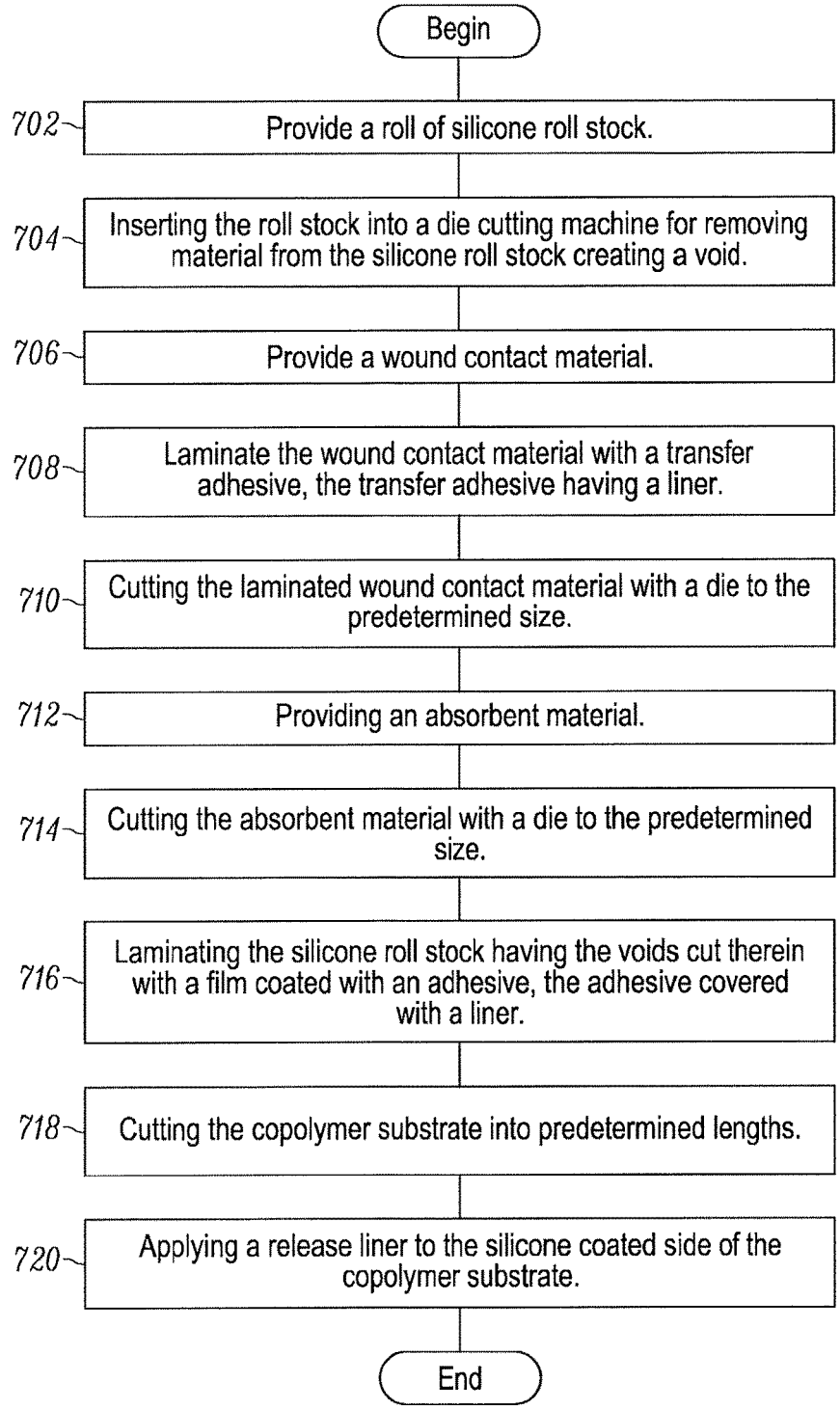
FIG. 7 is a flow diagram for one embodiment of a method for assembling a composite wound dressing.
Figure 8:
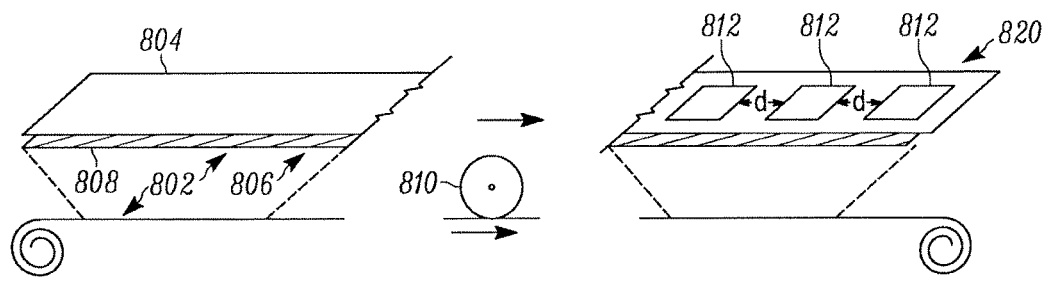
FIG. 8 is an exemplary process diagram of a machine for assembly of a composite wound dressing.
Figure 9:
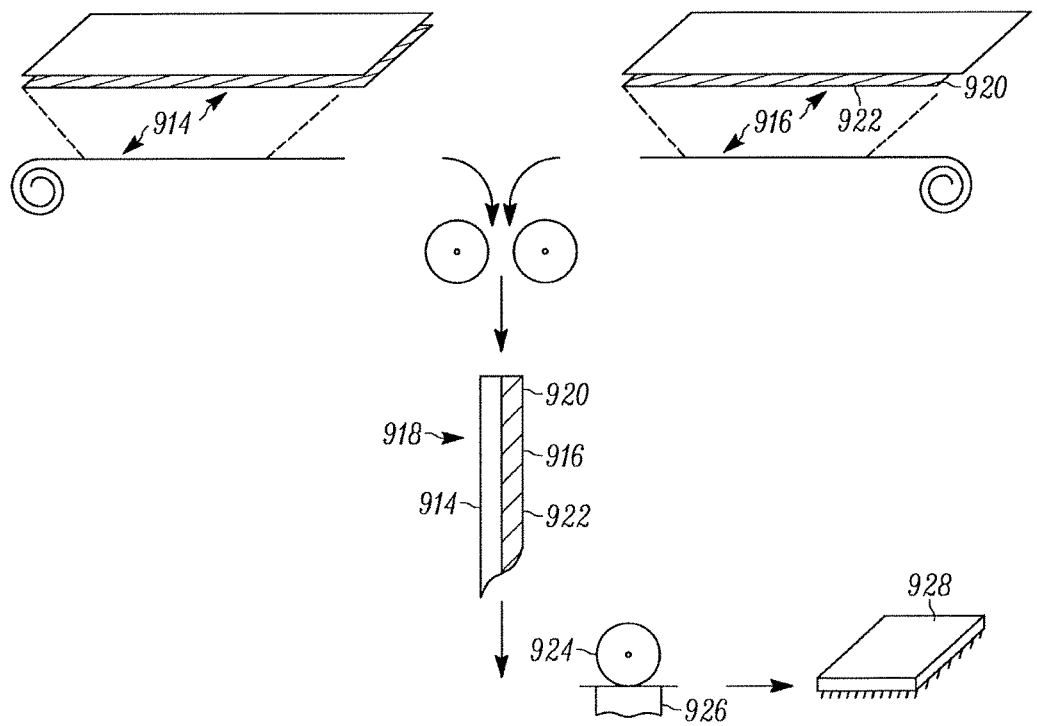
FIG. 9 is an exemplary process diagram of a machine for assembly of a composite wound dressing.
Figure 10:
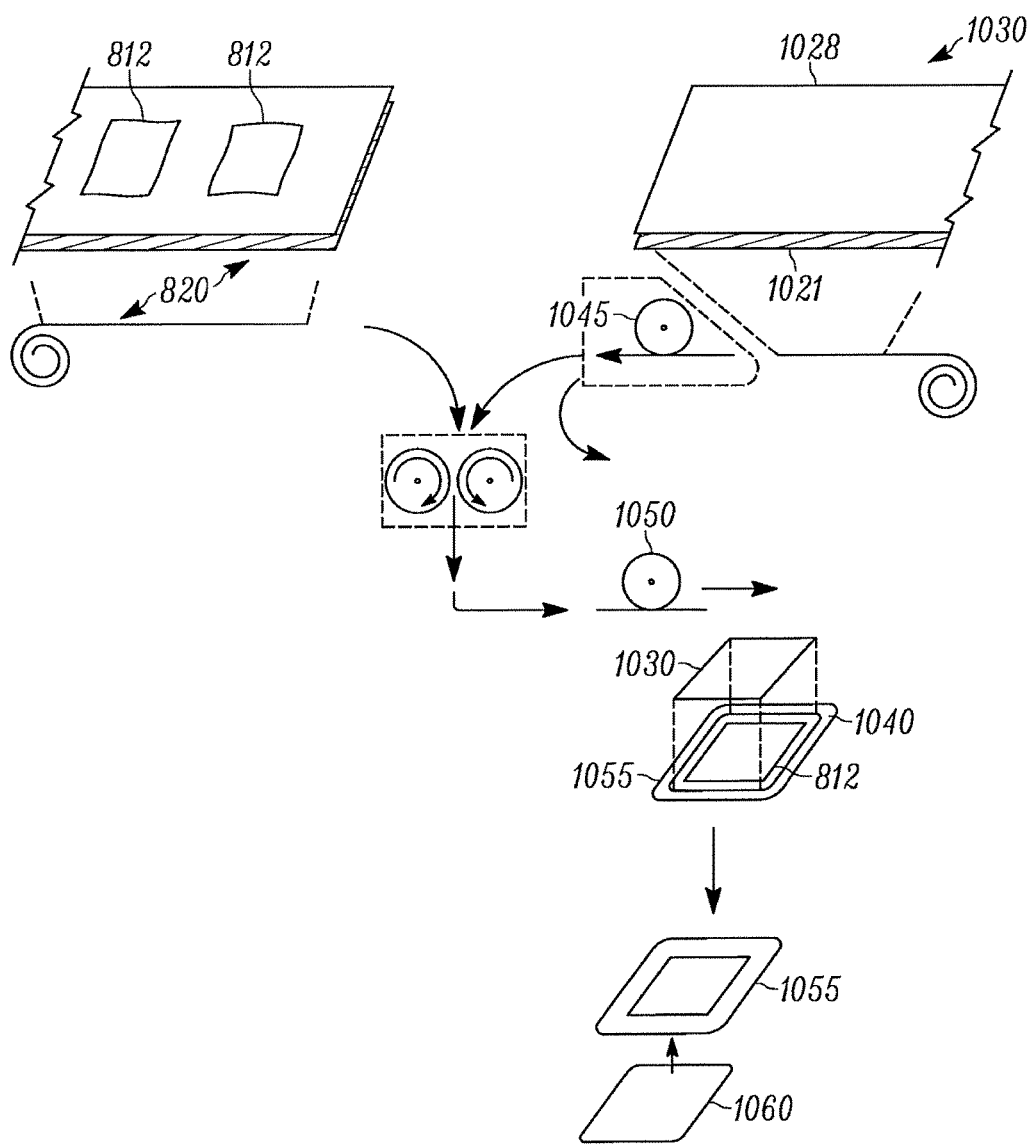
FIG. 10 is an exemplary process diagram of a machine for assembly of a composite wound dressing.

In one embodiment, illustrated in FIG. 6, the dressing comprises an absorbent material 608 configured between a first cushion layer 604 and a second cushion layer 602. The second foam layer 602 is configured between the backing layer 106 and the super absorbent layer 608.

In one exemplary embodiment, the composite wound dressing comprises a vapor permeable backing portion. An absorbent portion coupled to the vapor permeable backing with a first adhesive that is continuous or discontinuous. In one embodiment the MVTR of the absorbent portion is about 300 or more. A skin contact and securement portion coupled to the absorbent portion with a second discontinuous adhesive wherein. In one embodiment this second adhesive is a transfer adhesive. The skin securement portion is coupled to the backing portion, the skin securement portion including a semi-self adherent adhesive, and a void, wherein at least a portion of super absorbent is accessible through the void, and positioned within the void.

In another embodiment, a multilayer wound dressing comprises a top barrier layer which is a film, having a first side and a second side. A first discontinuous adhesive portion disposed on the first side of the barrier layer. A first cushion layer coupled to the first side of the barrier layer wherein at least one dimension of the cushion layer is less than a dimension of the barrier layer. A second discontinuous adhesive portion adjacent to the second side of the first cushion layer. An absorbent material substantially adjacent such that it may be horizontally and vertically centered relative to the barrier layer and may be centered relative to the first cushion layer. The absorbent material having dimensions such that at least one dimension is less than or equal to a dimension of the first cushion layer. A third discontinuous adhesive portion adjacent to the second side of the first cushion layer. A second cushion layer plannarly adjacent to the absorbent material substantially the same size as the first cushion, wherein the combination of the barrier layer, the first cushion layer, the second cushion layer, and the superabsorbent layer have a first MVTR. A border having a selectively adhesive coating, the border having a second MVTR, and the border having a void, wherein the absorbent material is configured within the void and the second cushion layer covers the void.

A method of making a wound dressing in one embodiment is illustrated in the flow diagram of FIG. 7 and FIGS. 8-10. The method of making the composite wound dressing comprises the steps of providing 702 silicone roll stock 802. The silicone roll stock 802 in this embodiment, comprises a copolymer substrate 804 coated on at least one side with a silicone based adhesive 806, and a first silicone liner 808 covers the silicone based adhesive. The silicone roll stock 802 is inserted to a die cutting machine 810, a rotary die cutting machine in this embodiment, for removing 704, by cutting or stamping out portions of the silicone roll stock leaving voids 812 in the roll stock 802 at predetermined intervals therein, a voided silicone roll stock 820.

A wound contact layer (WCL) 914 and a first transfer adhesive 916 are provided 706, both of which may be provided in roll stock form. The wound contact layer is laminated 708 with the first transfer adhesive 916 forming an adhesive coated WCL 918. The first transfer adhesive 916 in this embodiment is an acrylic adhesive 920 carried on a first transfer adhesive liner 922. The adhesive coated WCL 918 is then cut 710 into predetermined sizes. In one embodiment a rotary die 924 and anvil cuts 926 the adhesive coated WCL 918 to size, forming an absorbent chip 928. The first transfer adhesive liner 922 is removed for assembling the dressing or left in place until the adhesive coated WCL 918 is ready for assembly.

The method further comprises providing an absorbent material 712 and cutting 714 the absorbent material to a predetermined size, cutting in one embodiment the absorbent material from roll stock with a rotary die.

The silicone roll stock 820 with the voids 812 is laminated 716 with an acrylic adhesive coated polyurethane film 1030 having a first film liner 1028, such that the coated polyurethane film 1030 covers at least a portion of the void 812 in the silicone roll stock 820. The lamination process in this embodiment comprises mating the silicone roll stock 820 with the acrylic adhesive coated polyurethane film 1030. In one embodiment, the adhesive coated film 1030, which is cast on a film casting liner 1028, is unwound from a self-wound reel, just prior to die cutting the adhesive coated film 1030 to the predetermined size and prior to the mating of the film 1030 to the silicone roll stock 820. In this embodiment, the adhesive coated film 1030 is manually applied to the silicone roll stock 820. In another embodiment, the die cutting of the film 1030 may occur after the mating with the silicone roll stock 820. The first film liner 1028 is removed just prior to the packaging of the final product. In one embodiment, the coated polyurethane film 1030 has a size greater than the void 812 but less than an outer perimeter dimension of the cut to length silicone roll stock 1040 size. For example, in one embodiment, the void 812 is a square shape having a size of 2.625×2.625 inches and the polyurethane film 1030, after the film cutting process, has a size of 3.125×3.125 inches such that the polyurethane film 1030 overlaps the copolymer 1040, of the cut silicone roll stock 820 by 0.5 inches. In another embodiment, the copolymer substrate 1040 has a square size of 5.0×5.0 inches and the void 812 is a square having a size of 2.625×2.625 inches. The polyurethane film 1030 has a size of 5.0×5.0 inches such that the polyurethane film 1030 extends to the perimeter of the copolymer substrate 1040, substantially covering one side of the copolymer substrate 1040. It is advantageous in the first embodiment that the film 1030 does not extend to the edge of the copolymer substrate, as the dressing becomes less rigid and more pliable and comfortable to the user.

The processes further comprising cutting 718 the silicone roll stock 820 into predetermined lengths, which forms the outer perimeter of the securement layer formed by the silicone coated copolymer 820. In one embodiment, the copolymer 820 is cut to length after the step of laminating the copolymer 820 to the film 1030. In this embodiment, the copolymer 820 and the film 1030 are cut in the same cutting motion with a rotary die cutting machine 1050. In another embodiment, the film 1030 is cut with a separate die 1045 and then applied to the cut to length copolymer 820. Once the copolymer 820 and the film 1030 dressing portions are cut to finished size, forming a silicone copolymer film dressing portion 1055, a third release liner 1060 is applied 720 to the silicone side of the copolymer 820 of the dressing 100. In one embodiment, the third release line 1060 is a butterfly release liner which is configured to partially open giving access to the void and the adhesive of the film 1030.

In another embodiment the absorbent chip 928 having the absorbent material is coupled to the film 1030 within the void 812. The acrylic adhesive 1021 of the film 1030 secures the absorbent chip 928 to the film. In this embodiment, the acrylic adhesive is a discontinuous adhesive to allow the film 1030 to substantially retain its high MVTR characteristic. In another embodiment the acrylic adhesive is continuous, while still maintaining a moderate to high mvtr.

An absorbent material (not shown in FIGS. 8-10) is applied to the acrylic adhesive 1021 of the adhesive coated film 1030 such that the absorbent material is configured within the void 812. In one embodiment the absorbent material is placed onto the film 1030 through the opening in a butterfly release liner. In another embodiment, the absorbent material 1024 is placed on to the film 1030 prior to the butterfly release liner. The wound contact layer 118, which is a cushion layer, is coupled to the absorbent material, covers the entire void 225 and overlaps, on the outside of the dressing, the silicone coated copolymer 820 of the border layer.

Figure 11:
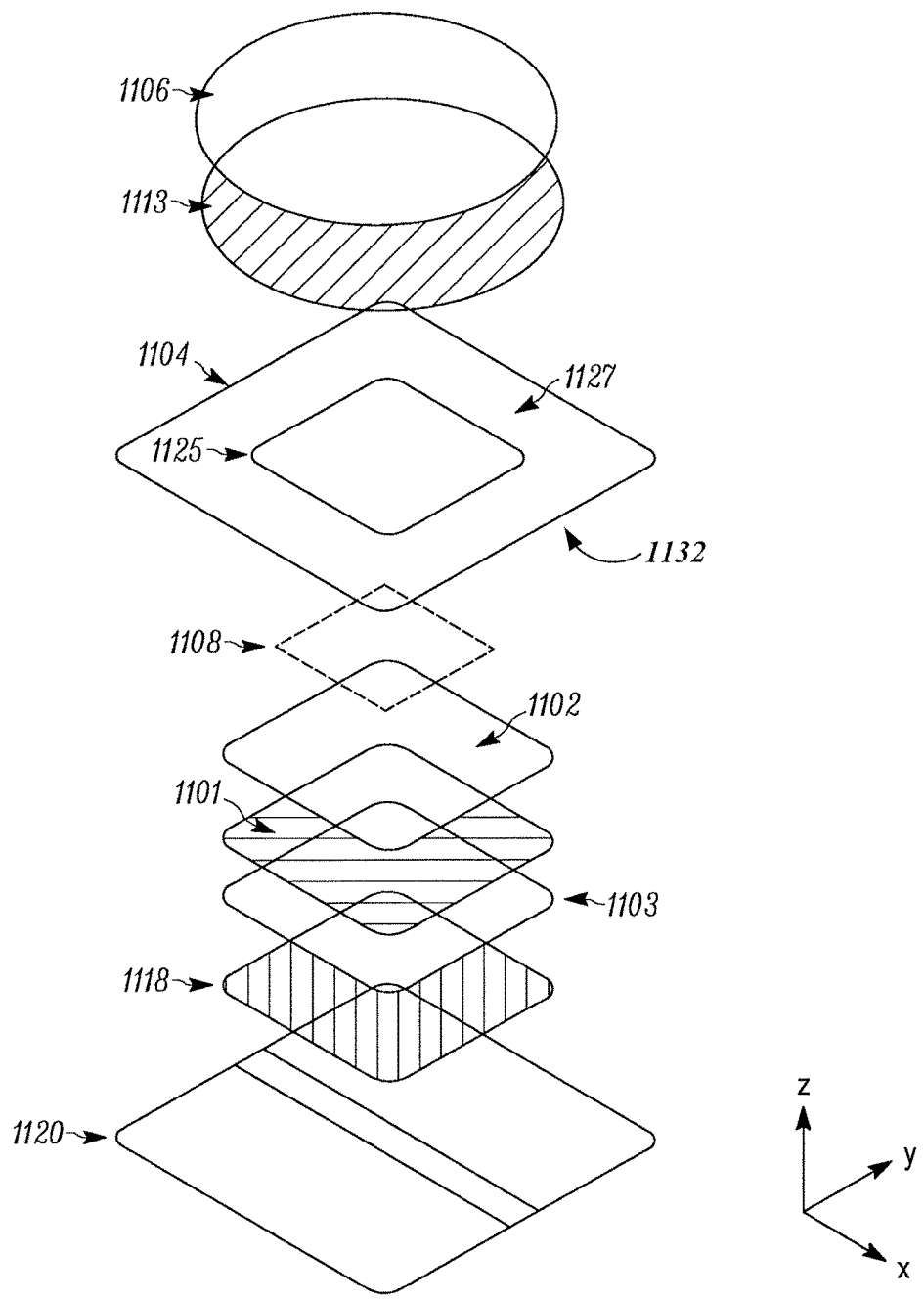
FIG. 11 is an exploded view of a composite wound dressing, according to an embodiment.

In one embodiment, illustrated in FIG. 11, an exploded view of another exemplary composite wound dressing 1100 is shown. In this embodiment a non-woven material 1101 is configured within the dressing so that it is positioned generally between a super absorbent 1108 material and a foam layer 1118. The non-woven provides rigidity to the foam 1118. In this embodiment, the non-woven material is a cellulose material. The cellulose material is preferably a 1.3 oz/square meter coated on both sides with 1.1 gm/100 sq-in pattern coated DM 1138 adhesive and with 78# differential liner. In another embodiment, a 1.5 oz/SY Chembonded nylon may be used, the nylon also coated both sides with 1.1 gm/100 sq-in pattern coated DM 1138 adhesive with 78# differential liner. Other non-woven materials used may include Polyester, polyamides, rayon, viscose rayon, cotton, polyurethane, polyethyelene, polypropylene and the like. Other weights, sizes and types of material that make up the non-woven may also be used so along as the characteristics do not significantly decrease the conformability of the dressing while on the user.

In this embodiment the foam 1118 thickness may be reduced, as a significant amount of the absorption occurs in the super absorbent 1108 portion of the dressing. The result is both reduced cost of the product as well the reduced overall dressing thickness, which is preferable from a patient comfort perspective. The non-woven adds support to the dressing allowing the foam to be thinner while still provide a skin-comfortable layer. In this embodiment, the foam has a thickness of $\frac{1}{16}^{th}$ of an inch.

Additionally, thin foam in general is difficult to manipulate in a continuous manufacturing process generally involving rotary presses. This is because the foam has very little structural strength and is difficult to manipulate, especially when coated with an adhesive (a transfer adhesive for example). The manufacturing process requires the manipulation of the foam to move the die cut foam/adhesive combination from one release liner to another surface, as is frequently done in rotary die cutting processes involving multiple layer dressings. The non-woven, attached to the foam with a patterned transfer adhesive, in one embodiment, allows the foam to retain the intended properties of the foam layer, such as porosity and absorption, yet eliminating some of the non desirable handling properties that complicate manufacturing, such as undue stretchiness and/or the difficulty inherent in moving a thin, non supported foam coated with an adhesive from one liner to another liner or surface.

The thickness of the foam 1118 in the z direction is $\frac{1}{16}$ of an inch in this embodiment with a dimension of 3.125 inches square size. In other embodiments the foam layer 1118 alone may be bigger in size or smaller in size, in at least one dimension, and is also scalable according to the overall size of the dressing. For example, scaling the overall size of the dressing up in size proportionally increases the size of the foam 1118 as well as the supper absorbent. The element sizing may also change un-proportionally to optimize skin adherence as well as absorbency as a function of dressing size.

The dressing in this embodiment also includes a backing layer 1106 having a diameter of at least 4 inches and in this embodiment is about 4.5 inches and preferably 4.63 inches. The backing layer 1106 has a first adhesive 1113, which may be a continuous or discontinuous adhesive, coated thereon. The backing layer 1106 is coupled to a border layer 1127 with the first adhesive 1113. In this embodiment the border layer has a larger overall outer dimension than the backing layer, however it may also have a smaller or equivalent dimension as well in other embodiments. The border layer has a skin contact side that has a second adhesive 1132 coated thereon. The border layer 1127 has a peripheral edge 1104 and an overall size of 5 inches square. The border layer 1127 has a void 1125 that has a size of 2.625 inches square. An absorbent layer 1108 is coupled to the barrier layer 1106 by the first adhesive 1113. The absorbent layer has a size of 2.0 inches square. In this embodiment the absorbent is a super absorbent material. The super absorbent layer is coupled to the non-woven layer 1101 by a third adhesive 1102 that lies between the two layers and distal to the foam layer 1118. A fourth adhesive 1103 adheres the non-woven layer 1101 to the foam layer 1118 on the proximate side of the non-woven layer 1101.

In this embodiment the third adhesive 1102 and the fourth adhesive 1103, are transfer adhesives and promote the securement of the plurality of layers of the composite wound dressing 1100. A release liner 1120, which is a "butterfly" liner in this embodiment is made up of two overlapping parts is removably applied to the dressing, adhering to the second adhesive, covering the dressing on one side in its entirety.

Figure 12:
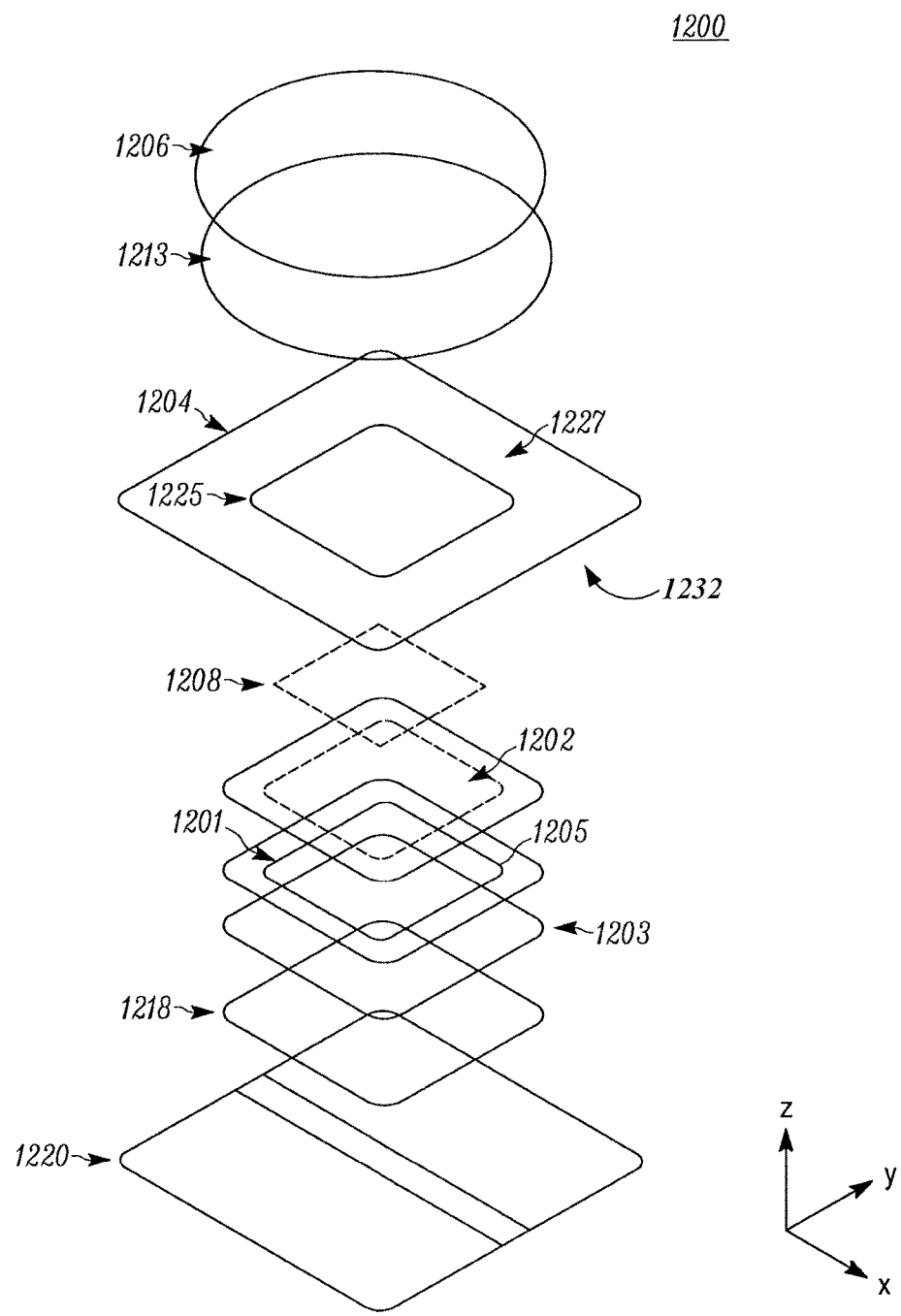
FIG. 12 is an exploded view of a composite wound dressing, according to an embodiment.

In yet another embodiment, illustrated in FIG. 12, an exploded view of another exemplary composite wound dressing 1200 is shown. In this embodiment a non-woven material 1201 has a frame shape and is configured within the dressing so that it is positioned generally between a super absorbent 1208 material and a foam layer 1218. The non-woven frame 1201 provides rigidity to the foam 1218, however, allows for a greater flow rate of fluid from the foam 1218 to the superabsorbent material 1208. In this embodiment, the non-woven material is a cellulose material. The cellulose material is preferably a 1.3 oz/square meter coated on both sides with 1.1 gm/100 sq-in pattern coated DM 1138 adhesive and with 78# differential liner. The non-woven has a void 1205 therein wherein the size of the void 1205 has a dimension that is less than the outer dimension of the non-woven layer itself. Other weights, sizes and types of material that make up the non-woven may also be used so along as the characteristics do not significantly decrease the conformability of the dressing while on the user.

The dressing in this embodiment also includes a backing layer 1206 has a diameter of at least 4 inches and in this embodiment is about 4.5 inches and preferably 4.63 inches. The backing layer 1206 has a first adhesive 1213, which may be a continuous or discontinuous adhesive, coated thereon. The backing layer 1206 is coupled to a border layer 1227 with the first adhesive 1213. In this embodiment the border layer 1227 has a larger overall outer dimension than the backing layer 1206, however it may also have a smaller or equivalent dimension as well in other embodiments. The border layer 1227 has a skin contact side that has a second adhesive 1232 coated thereon. The border layer 1227 has a peripheral edge 1204 and an overall size of 5 inches square.

The border layer 1227 has a void 1225 that has a size of 2.625 inches square. An absorbent layer 1208 is coupled to the barrier layer 1206 by the first adhesive 1213. The absorbent layer has a size of 2.0 inches square. In this embodiment the absorbent is a super absorbent material. The super absorbent layer is coupled to the non-woven layer 1201 by a third adhesive 1202 that lies between the two layers and distal to the foam layer 1218. The third adhesive layer 1202 may have the same shape as the non-woven, i.e. with a void, as they are generally cut together in the manufacturing process or the adhesive may be one continuous layer. The same is true for the fourth adhesive 1203. The fourth adhesive 1203 adheres the non-woven layer 1201 to the foam layer 1218 on the proximate side of the non-woven layer 1201. A release liner 1220, which is a "butterfly" liner in this embodiment, is made up of two overlapping parts removably applied to the dressing, adhering to the second adhesive, covering the dressing on one side in its entirety.

Designs of the non-woven other than the solid non-woven design as well as the window frame design can be replaced by other configuration, for example a cross shaped design of the transfer adhesive on the cellulosic non-woven (which itself may be cross shaped corresponding with the transfer adhesive shape. Alternatively, the non-woven x and y dimensions may be larger than the cross shaped adhesive overall dimensions.

While the present disclosure and the best modes of the inventions have been described in a manner establishing possession hereof by the inventors and enabling those of ordinary skill in the art to make and use the same, it will be understood and appreciated that there are many equivalents to the exemplary embodiments disclosed herein and that modifications and variations may be made thereto without departing from the scope and spirit of the inventions, which are to be limited not by the exemplary embodiments but by the appended claims.

What is claimed is:

1. A composite wound dressing comprising:
    a vapor permeable backing portion;
    a super absorbent portion coupled to the vapor permeable backing portion with a first adhesive;
    a wound contact portion having a first portion coupled to the super absorbent portion with a second adhesive, and the wound contact portion having a second portion that is directly coupled to the vapor permeable backing portion with the first adhesive; and
    a skin securement portion coupled to the vapor permeable backing portion with the first adhesive, the skin securement portion including a semi-self adherent adhesive, and a void having a first size,
    wherein at least a portion of the super absorbent portion is accessible through the void, and
    wherein the wound contact portion has a size greater than the first size of the void.

2. The wound dressing of claim 1, wherein the skin securement portion comprises a planar sheet having a void, the void first size defined by at least two dimensions.

3. The wound dressing of claim 2, wherein the vapor permeable backing portion has a size greater in at least one dimension than the first size of the void of the skin securement portion.

4. The wound dressing of claim 1, wherein the skin securement portion has a first MVTR.

5. The wound dressing of claim 4, wherein the super absorbent portion has an MVTR greater than the first MVTR of the skin securement portion.

6. The wound dressing of claim 1, wherein at least a portion of the skin securement portion is configured between the wound contact portion and the vapor permeable backing portion.

7. The wound dressing of claim 6, wherein the vapor permeable backing portion is coupled to a portion of the super absorbent portion, a portion of the wound contact portion and a portion of the skin securement portion.

8. The wound dressing of claim 1, wherein the vapor permeable backing portion is substantially liquid impervious.

9. The wound dressing of claim 1, wherein the semi-self adherent adhesive is adjacent to the wound contact portion.

10. The wound dressing of claim 1, wherein the wound contact portion is polyurethane foam.

11. The wound dressing of claim 1, wherein the wound contact portion has at least one dimension greater than the size of the void of the skin securement portion.

12. The wound dressing of claim 1, wherein the wound contact portion extends from within the void of the skin securement portion such that a non wound facing side of the wound contact portion is adjacent to at least a portion of a skin contact side of the skin securement portion.

13. The wound dressing of claim 1, wherein the vapor permeable backing portion extends only over the void and adjacent to the super absorbent portion.

14. The wound dressing of claim 1, wherein the vapor permeable backing portion has a size that is the same as a size as the skin securement portion.

15. The wound dressing of claim 1, wherein the wound contact portion is a swellable foam material comprising polyurethane.

16. The composite wound dressing of claim 1, wherein the skin securement portion includes a skin contacting side and a backing layer contacting side, the wound contact portion being coupled to the skin contacting side of the skin securement portion.

17. A composite dressing comprising:
a backing layer;
an absorptive portion comprising a first continuous adhesive, a super absorbent material having super absorbent polymers, a second discontinuous adhesive, and a foam layer, wherein the first continuous adhesive is coupled between the super absorbent material and the backing layer; and
a skin securement layer including a void having a size greater than a size of the absorptive portion.

18. The composite dressing of claim 17, wherein the super absorbent material is disposed within the void of the skin securement layer.

19. The composite dressing of claim 17, wherein the skin securement layer includes a skin contacting side and a backing layer contacting side, the foam layer being coupled to the skin contacting side of the skin securement layer.

20. A wound dressing comprising:
a continuous film layer;
a layer of a pattern-coated acrylic first adhesive carried on the film layer;
a border layer of copolyester having a void cut therein, the border layer having a first side and a second side distal to the first side;
a continuous second adhesive layer comprising silicone carried on the first side of the copolyester layer,
wherein the first side is a skin contact side;
an absorbent portion configured within the void and coupled by the first adhesive to the film layer;
a foam layer that covers the void and is coupled to the absorbent portion with a third adhesive, and
wherein the foam layer is coupled to the film layer with the first adhesive, and
wherein the foam layer overlaps the border layer near an edge of the void; and
a release liner.

21. The wound dressing of claim 17, wherein the foam layer overlaps the border layer near the edge of the void such that the foam layer is directly coupled to the first side of the border layer.

* * * * *